United States Patent [19]
Helderman

[11] Patent Number: 5,773,722
[45] Date of Patent: Jun. 30, 1998

[54] TORQUE ACTUATED TENSILE TESTER

[76] Inventor: James F. Helderman, 414 S. Maple St., Graham, N.C. 27253

[21] Appl. No.: 367,947

[22] Filed: Jan. 3, 1995

[51] Int. Cl.$^6$ .................................................. G01N 3/08
[52] U.S. Cl. ................................ 73/826; 73/786; 73/803; 73/817
[58] Field of Search ............................ 73/761, 786, 788, 73/796, 803, 817, 826, 856, 858

[56] References Cited

U.S. PATENT DOCUMENTS

| | | | |
|---|---|---|---|
| 3,283,566 | 11/1966 | Fietz . | |
| 3,403,594 | 10/1968 | Newell . | |
| 3,533,284 | 10/1970 | Slemmons et al. | 73/817 |
| 3,640,126 | 2/1972 | Te'eni | 73/803 |
| 3,643,500 | 2/1972 | Anderson | 73/803 |
| 3,803,907 | 4/1974 | Ryckman et al. | 73/817 |
| 4,103,540 | 8/1978 | McLaughlin | 73/803 |
| 4,425,801 | 1/1984 | Stoll | 73/803 |
| 4,471,662 | 9/1984 | Hamilton | 73/788 |
| 4,501,153 | 2/1985 | Mehes et al. | 73/803 |
| 4,748,855 | 6/1988 | Barnoff | 73/803 |
| 5,345,826 | 9/1994 | Strong | 73/826 |
| 5,479,830 | 1/1996 | Gemra | 73/826 |

OTHER PUBLICATIONS

"Proof Load Tester—Instruction Data", one page.

*Primary Examiner*—George M. Dombroske
*Attorney, Agent, or Firm*—Kennedy Covington Lobdell & Hickman L.L.P.

[57] ABSTRACT

A torque actuated tensile tester for proof loading anchors includes: an actuator, a left hand square nut, a right hand jam nut, an anchor head carrier, a housing, a slip gauge, and a keeper clip. The actuator has a cross-threaded portion and a portion engageable by a torque applying member. The housing has first and second ends, with the first end positionable circumjacent the anchor to be proof loaded and that is engageable with the structure to which the anchor is affixed. The left hand square nut is internally threaded with a single left hand thread that is engageable with the threaded portion of the actuator. The right hand jam nut is internally threaded with a single right hand thread that is engageable with the threaded portion of the actuator. The anchor head carrier is internally threaded with a single right hand thread that is engageable with the threaded portion of the actuator. The anchor head carrier has a flanged slot for receiving the head of an anchor for engagement. The right hand jam nut, the left hand square nut, and the anchor head carrier are threadedly attached to the actuator in use, and the threaded assembly is inserted into the housing. The left hand square nut is attachable to the second end of the housing when an anchor is engaged by the anchor head carrier. Furthermore, when the anchor is engaged by the anchor head carrier and a predetermined torque is applied to the engageable portion of the actuator by a torque applying member, the actuator tends to turn, thereby urging the anchor head carrier towards the left hand square nut, and in turn, applying a tensile force to the anchor. The left hand square nut transmits an equal and opposite force to the tensile force through the housing to the structure circumjacent the anchor, providing that the anchor does not slip. A slip gauge rests upon the anchor head carrier and indicates the extent of movement, if any, of the anchor head carrier with respect to the left hand square nut. A keeper dip is attached to the housing to secure the actuator, right hand jam nut, left hand square nut, and anchor head to the housing.

22 Claims, 6 Drawing Sheets

TORQUE ACTUATED TENSILE TESTER

BACKGROUND OF THE INVENTION

The present invention relates to a device for converting torque into tensile force, and more particularly, to a device for converting torque into tensile force for testing the tensile strength of anchors and the like anchored in steel and concrete structures and the like.

The tensile strength of an anchor should be determined before use to ensure that the anchor load limit is not exceeded, which could result in slippage or failure of the anchor. Often, anchors must meet certain specifications pursuant to building codes. However, sometimes anchors are installed into brick-work or stone-work for which no specifications were ever determined, especially in older buildings and structures, and at other times a reevaluation of old anchors is required even if the original specifications of such anchors was known.

Over a long period of time various methods have been used to test the resistance of anchors and the like to slippage or failure. These methods have ranged from the physical application of weights to anchors, to the use of simple and complex devices and machines including fulcrum and lever, hydraulic pumps, and spring dynamometers. One disadvantage to using such devices and machines is that, for the most part, they are bulky and awkward to use in job-site situations because of limited space and awkwardness of operation, usually requiring two or more people to conduct the required testing.

Each machine and device also exhibits its own peculiar drawbacks in operation. For example, hydraulic jacks are sometimes inaccurate in testing ultimate loads. When testing the "pullout" resistance of anchors with hydraulic jacks, the check valve between the hydraulic pump and jack can sometimes leak, allowing a flow back of hydraulic fluid into the pump and causing the pressure gauge to fall. This can be interpreted as slippage of the anchor under test. Continued pumping can subsequently cause corresponding rising and falling of the pressure gauge, and it is not always immediately known if the anchor is slipping or if hydraulic fluid is actually flowing back into the pump. Sometimes both conditions occur. In any event, it is difficult to accurately determine the exact amount of anchor slippage or the load under which slippage first occurred.

Conventional torque devices are seldom used in testing the tensile strength of anchors because of the difficulty in separating torsional and tensile forces; the totality of the input energy results from a rotational force, yet anchors are usually only subjected in use to tensile or shear forces. Conventional torque devices cannot convert torque applied to such devices into tensile force applied to anchors without application of a rotational force also being applied to the anchors, thereby making accurate load determination difficult.

For these reasons, most anchor testing is conducted in laboratories where space and the complicated operation of bulky devices and machines present less of a problem than job-site testing impose. Furthermore, the cost of such job-site testing is usually prohibitively expensive. Nevertheless, such awkward devices and machines are in fact used at great expense in job-site testing where remote laboratory testing is infeasible or not acceptable.

Laboratory testing is not an ideal solution, however. For example, it is customary to test concrete anchors under laboratory conditions where the concrete conforms to design mix standards which are intended to produce certain strength levels. The wet mix is then placed and cured under idealized laboratory conditions. Afterwards, at chronological intervals, a series of holes are drilled in the test slab and concrete anchors are installed into the holes and subjected to tensile pullout loading. The average of these tests to failure is then called the "ultimate load." Then a safety factor is applied by dividing the "ultimate load" by that factor. The resulting numerical figure is then called a "safe working load" that should not be exceeded when the anchor is used. When anchors are installed in the field, however, they are not always installed by the most knowledgeable mechanics, and thus the laboratory results often do not accurately predict the true tensile strength of anchors used at a particular job-site. Discrepancies arise when concrete anchors are used, for instance, from the fact that concrete into which the anchors are installed have many variables that can differ from the laboratory conditions under which the anchors are subjected to testing. For example, the field concrete may be four weeks old, or fifty years old; the strength of the slab may or may not be known; and coarse and fine aggregate types and sizes are probably much different from that found in the laboratory slab. There also is no guarantee that the wet concrete was properly mixed, placed, vibrated or cured, or that additional water was not used by the workmen at the time the concrete was placed, which would substantially change the water-ement ratio. All of these and other variables put into question the reliability of the so called "safe working load" derived in a laboratory with respect to the tensile strength of anchors at a particular job-site.

SUMMARY OF THE INVENTION

It is thus an objective of the present invention to provide a device for testing the tensile strength of anchors and the like anchored in steel and concrete structures and the like in a simple and inexpensive manner at the job-site where the anchors are used.

Briefly described, the present invention is an improvement over conventional devices used for testing the tensile strength of anchors. The present invention includes an actuator, a support member, means on the support member for supporting the actuator, and means on the actuator for engaging an anchor to be proof loaded. The actuator has at least one threaded portion and a portion that is engageable by a torque applying member. The support has an end that is positionable adjacent the anchor to be proof loaded and that is engageable with the concrete or steel structure, or the like, in which the anchor to be proof loaded is affixed. It is also contemplated that the support member need only be positionable in a rigid position with respect to the structure in which the anchor to be proof loaded is affixed, and that it need not be engageable directly with the structure in which the anchor to be proof loaded is affixed. The support means on the support member supports the actuator for rotation in alignment with the anchor to be proof loaded. The engaging means is connected to the actuator in a manner that allows the actuator to rotate with respect to the anchor to be proof loaded, is movable with respect to the support member, and is locatable at a spacing from the supporting means. At least one of the at least one threaded portion of the actuator is threadedly engaged with at least one of the supporting means and the engaging means for movement of the engaging means towards the supporting means upon rotation of the actuator in one direction by application of a torque to the engageable portion of the actuator by a torque applying member. Thus, when the anchor to be proof loaded is engaged by the engaging means and a predetermined torque is applied to the engageable portion of the actuator by a torque applying member, a predetermined proof load is applied to the anchor.

A feature of the present invention includes means supported on one of the supporting means and engaging means that is movable with respect to the other of the supporting means and engaging means for indicating an extent of movement of the engaging means with respect to the supporting means.

A further feature of the present invention includes means for locking the actuator in a fixed position with respect to the supporting means in order to sustain a fixed proof load on the anchor over an extended period of time.

A yet further feature of the present invention includes means engageable with the support member for securing the actuator, the supporting means, and the engaging means to the support member when inverted.

Another feature of the present invention includes a torque applying member that is engageable with the engageable portion of the actuator.

In one variation of the present invention, at least one of the at least one threaded portion of the actuator is threadedly engageable with the supporting means. In another variation, at least one of the at least one threaded portion of the actuator is threadedly engageable with the engaging means. In yet another variation, at least one of the at least one threaded portion of the actuator is threadedly engageable with the supporting means and at least one of the at least one threaded portion of the actuator is threadedly engageable with the engaging means. In a fourth variation, at least one of the at least one threaded member of the actuator is threadedly engageable with both the supporting means and the engaging means, the supporting means and the engaging means are oppositely threaded, i.e., one has a left hand thread and one has a right hand thread, and the at least one of the at least one threaded portion of the actuator is cross-threaded with left hand and right hand threads.

In another variation, when the present invention includes a locking means, at least one of the at least one threaded portion of the actuator is threadedly engageable with the locking means and the supporting means, with the locking means oppositely threaded with respect to the supporting means for threadedly locking the locking means and the actuator to the supporting means when the locking means is adjacent the supporting means.

The present invention is susceptible to a broad range of uses. In this respect, the present invention is well suited for measuring the weight of an object, and particularly suited for measuring the weight of an object that is to be attached to an anchor that can be proof loaded by the present invention.

Thus, another feature of the present invention, applicable to using the present invention for measuring the weight of an object to be attached to an anchor that can be proof loaded, includes means secured to the support member for fixedly mounting the support member above the object to be weighed, and means for connecting the engaging means with the object to be weighed. Thus, when the object to be weighed is engaged by the connecting means, which is attached to the engaging means, the application of a torque to the engageable portion of the actuator by a torque applying member causes the engaging means to move towards the supporting means to suspend the object to be weighed, the torque applied to suspend the object being directly proportional to the weight of the object.

Generally, the present invention as previously described, recast in the light of a weighing device, includes an actuator, a support member, supporting means on the support member for supporting the actuator, and means on the actuator for engaging the object to be weighed. The actuator has at least one threaded portion and a portion that is engageable by a torque applying member. The support member is attachable to a fixed structure. The supporting means on the support member supports the actuator for rotation about a vertical axis. The engaging means is connected to the actuator in a manner that allows the actuator to rotate, is movable with respect to the support member, and is locatable at a spacing from the supporting means. At least one of the at least one threaded portion of the actuator is threadedly engageable with at least one of the supporting means and the engaging means for movement of the engaging means towards the supporting means upon rotation of the actuator in one direction by application of a torque to the engageable portion of the actuator by a torque applying member. Thus, when the object to be weighed is engaged by the engaging means, the application of a torque to the engageable portion of the actuator by a torque applying member causes the engaging means to move towards the supporting means to suspend the object to be weighed, the torque applied to suspend the object being directly proportional to the weight of the object.

The further features of the present invention are also applicable to the present invention when recast in the light of a weighing device. For example: at least one of the at least one threaded portion of the actuator can be threadedly engageable with the supporting means; at least one of the at least one threaded portion of the actuator can be threadedly engageable with the engaging means; at least one of the at least one threaded portion of the actuator can be threadedly engageable with the supporting means and at least one of the at least one threaded portion of the actuator can be threadedly engageable with the engaging means; and at least one of the at least one threaded portion of the actuator can be threadedly engageable with both the supporting means and the engaging means, with the supporting means and the engaging mean oppositely threaded, and the at least one of the at least one threaded portion of the actuator cross-threaded with left hand and right hand threads.

BRIEF DESCRIPTION OF THE DRAWINGS

The torque actuated tensile tester of the present invention may best be understood with reference to the following drawings, wherein.

DETAILED DESCRIPTION OF THE PREFERRED EMBODIMENT

Figure 1:
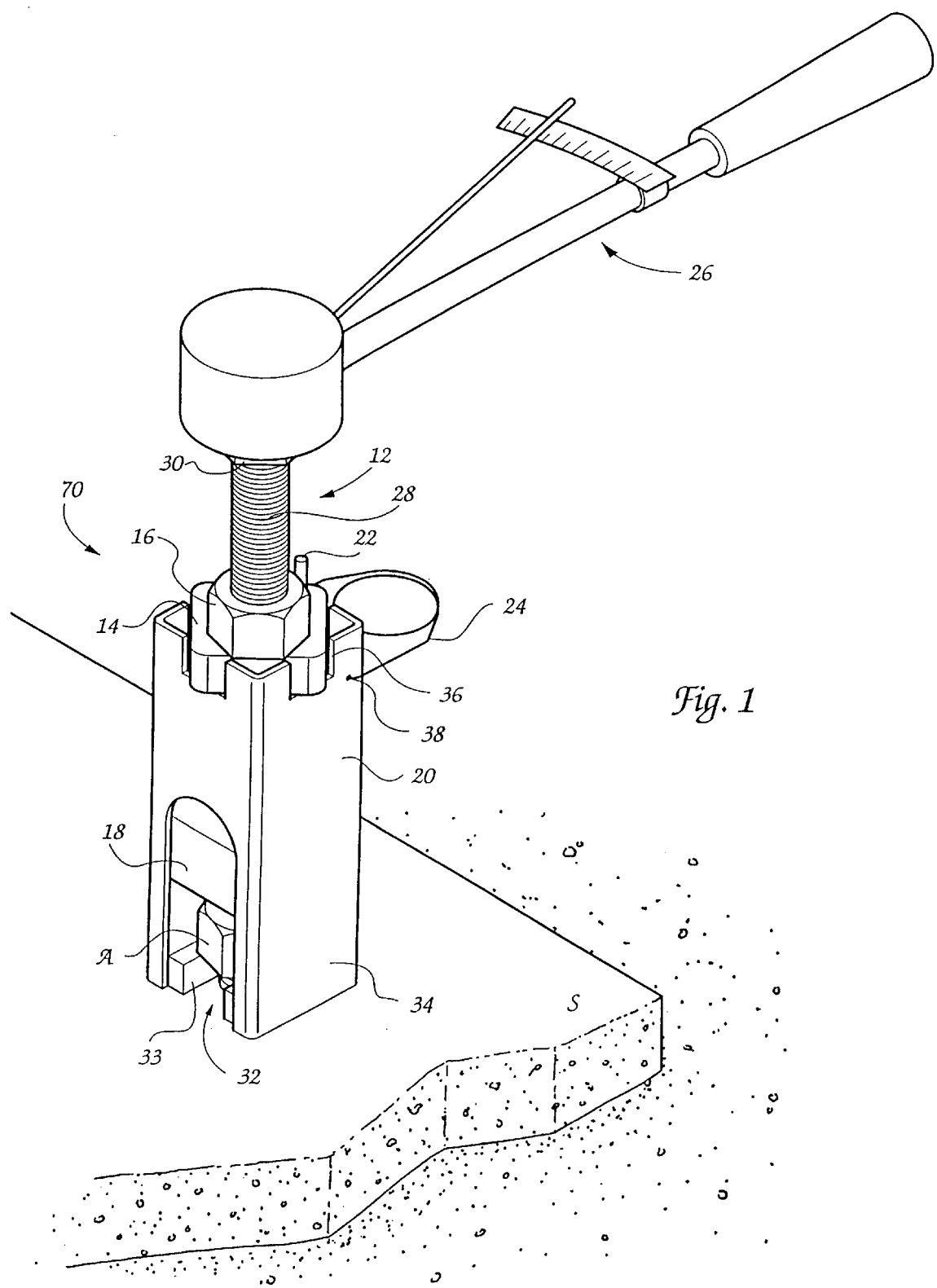
FIG. 1 is a perspective environmental view of a torque actuated tensile tester according to the preferred embodiment of the present invention.

Referring now to the preferred embodiment as disclosed in FIGS. 1–6, the torque actuated tensile tester 10 of the present invention includes an actuator 12, supporting means in the form of a left hand square nut 14, locking means in the form of a right hand jam nut 16, engaging means in the form of an anchor head carrier 18, a support member in the form of a housing 20, indicating means in the form of a slip gauge 22, and securing means in the form of a keeper clip 24.

The actuator 12 resembles a bolt; it has an elongated threaded portion 28 and a portion 30 in the form of a hexagonal head engageable by a torque wrench 26 as illustrated in FIG. 1. The threaded portion 28 of the actuator 12 is externally cross-threaded with both left hand and right hand threads, 46 and 48 respectively, illustrated in FIG. 5. The housing 20 is also elongated and has an end 34 that is positionable circumjacent the anchor to be proof loaded and that is engageable with the concrete structure S, or the like, in which the anchor is affixed. The left hand square nut 14 is internally threaded with a left hand thread 15 that is threadedly engageable with the threaded portion 28 of the actuator 12. The right hand jam nut 16 is internally threaded with a right hand thread 17 that is threadedly engageable with the threaded portion 28 of the actuator 12. The anchor head carrier 18 is internally threaded with a right hand thread 19 that is threadedly engageable with the threaded portion 28 of the actuator 12. The right hand thread 19 of the anchor head carrier 18 is approximately the thread-root diameter of the threaded portion 28 of the actuator 12. The anchor head carrier 18 has a flanged slot 32 for receiving the head A' of an anchor A for engagement. A smooth bore 58 is provided between the right hand thread 19 and the flanged slot 32 where the anchor head A' is engaged. If a threaded anchor does not have a head, or an anchor head is too small for engagement by the anchor head carrier 18, an adapter can be attached to the anchor for proper fit in the flanged slot 32. Such adapters can include, among other possibilities, adapters that are slotted and horseshoe shaped, or simply washers. A slip gauge 22 is provided for indicating the extent of movement of the anchor head carrier 18 with respect to the left hand square nut 14. The keeper clip 24 is provided in the form of a wire spring.

Figure 2:
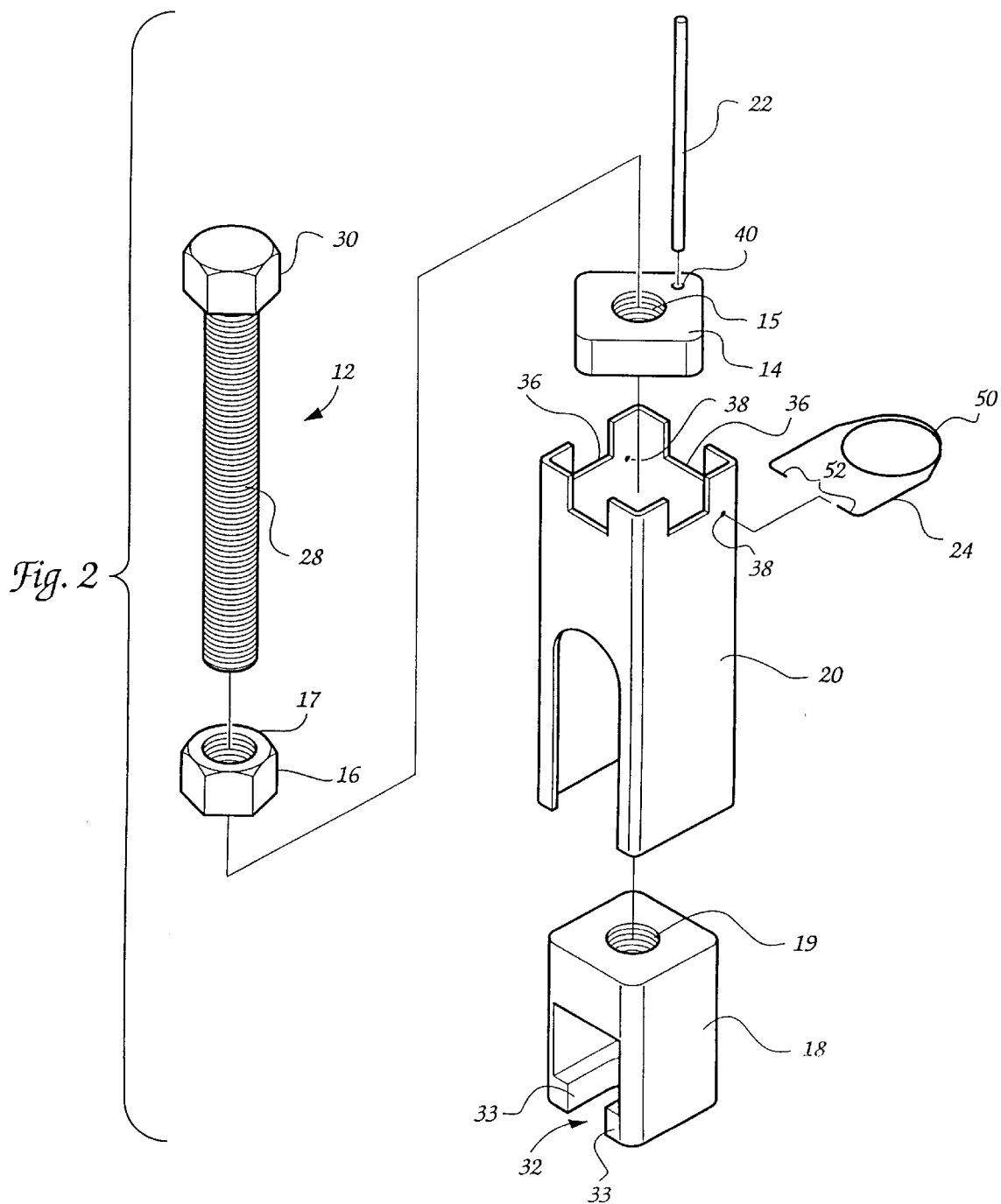
FIG. 2 is an exploded view of the torque actuated tensile tester of FIG. 1.
Figure 3:
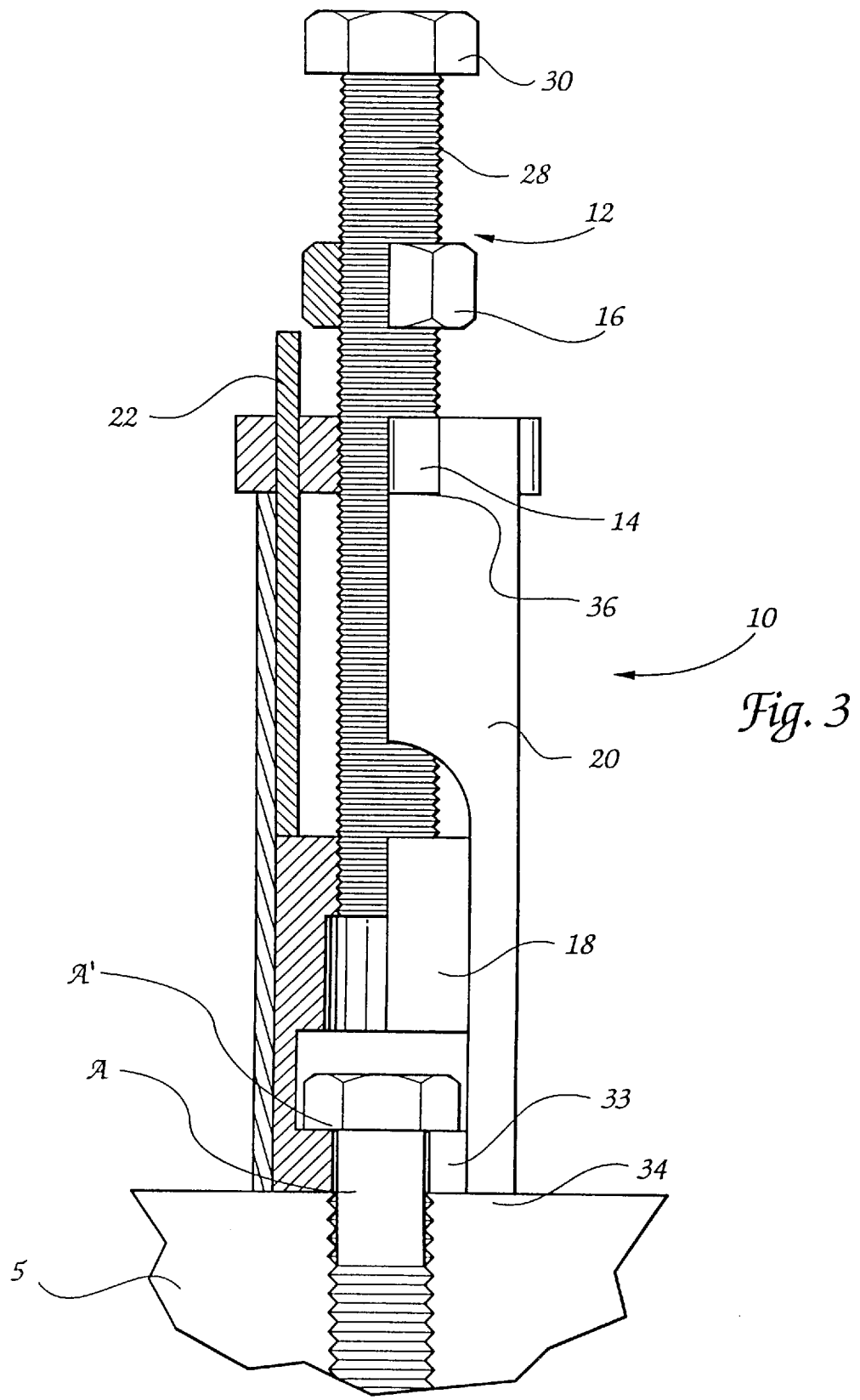
FIG. 3 is an elevational view, partially in broken away cross-section, of the torque actuated tensile tester of FIG. 1.

The seven parts of the preferred embodiment may be assembled by first screwing the internally threaded parts, i.e., the right hand jam nut 16, the left hand square nut 14, and the anchor head carrier 18, in their respective positions as schematically shown in FIG. 2 onto the cross-threaded portion 28 of the actuator 12. In attaching the last threaded member, i.e., the anchor head carrier 18, the threaded portion 28 of the actuator 12 should be threadedly engaged with all of the right hand thread 19 of the anchor head carrier 18, as shown in FIG. 3. This provides a constant frictional resistance between the threaded portion 28 of the actuator 12 and the right hand thread 19 of the anchor head carrier 18 during movement of the anchor head carrier 18 towards the left hand square nut 14, since a smooth bore 58 provides no frictional resistance to the threaded portion 28 of the actuator 12 as the anchor head carrier 18 advances towards the left hand square nut 14. Once the threaded members have been assembled, they then can be inserted into the housing 20, or the threaded assembly can first be coupled with an anchor, in which case, the housing 20 can then be placed over the assembled threaded parts by sliding the housing 20 over them. When the housing 20 is in position, the left hand square nut 14 is turned in a diagonal direction relative to the housing 20, and by rotating and adjusting the actuator 12 by hand, the corners of the left hand square nut 14 may be properly seated into the castleated slots 36 of the housing 20.

The assembled threaded parts will easily slide out of the housing 20 if the torque actuated tensile tester 10 of the present invention is inverted or is picked up and carried in an upside down position. To prevent spilling the assembled threaded parts from the housing 20, the keeper clip 24 is attached to the housing 20 by inserting the ends 52 of the keeper clip 24 into two holes 38 in the housing 20. Furthermore, the keeper clip 24 is formed with a loop 54 not only to insure resilience of the keeper clip 24, but also to insure safety; when testing sidewall or overhead anchor installations, one end of a safety line may be tied through the loop 54 of the keeper clip 24 and the other end of the safety line secured to some other object such as another anchor, pipe, or scaffold, just in case the anchor being tested should break or pullout.

To use torque actuated tensile tester 10 for proof load testing, the anchor A to be tested is installed in any required location. Then the exposed head A' of that anchor A is fitted into the flanged slot 32 of the anchor head carrier 18 with the flanges 33 of flanged slot 32 extending under the anchor's head A', as seen in FIG. 3. The engageable portion 30 of the actuator 12 is then turned clockwise by hand until all slack between threaded parts and the anchor is taken up. The torque actuated tensile tester 10 and anchor are now ready for the application of a known and predetermined proof load by way of application of a corresponding known and predetermined torque to the engageable portion 30 of the actuator 12. Thus, when the anchor head carrier 18 is in engaging contact with the anchor A to be proof loaded, and a predetermined torque is applied, the actuator 12 will tend to turn. The castleated slots 36 prevent the left hand square nut 14 from sliding through the housing 20 and lock the left hand square nut 14 in a fixed rotational position with respect to the housing 20. Thus, when the actuator 12 turns, the castleated slots 36 prevent the left hand square nut 14 from also turning, thereby transferring to the housing 20, and subsequently to the structure S to which the anchor A is attached, a compressive force, and thereby allowing the anchor head carrier 18 to be urged towards the left hand square nut 14, resulting in a tensile force being applied to the anchor A.

It is contemplated that the housing 20 need not be engageably positionable adjacent the anchor A. For example, the torque actuated tensile tester could be attached to another structure that is rigid with respect to the structure S in which the anchor A is affixed, or alternatively, it could be supported by a bridge member extending over the anchor to be tested, with the bridge member positionably engageable with the structure S in which the anchor is affixed but not adjacent the anchor (not shown). In any event, the present invention only requires that the torque actuated tensile tester be maintained in a rigid position with respect to the anchor to be proof loaded during testing, and that the engaging means be in a position to be engageable with the anchor head to be tested.

In testing for the safe load carrying ability of anchors it is also important to test for slippage of the anchor under load. For example, sometimes it is found that while a concrete slab may have adequate compressive strength to carry its required dead and live loads, it may have insufficient strength to sustain an anchor in a point loaded position or condition, which is normal for substantially all anchored loads, concrete course and fine aggregates being at times too friable to offer the frictional resistance to slippage an anchor requires over extended periods of time.

A simple slip gauge 22 is provided in the preferred embodiment of the torque actuated tensile tester 10 to indicate slippage. A hole 40 is drilled through the left hand square nut 14 located about midway between the edge of the internal left hand thread 15 and one of the corners of the square nut 14. When the apparatus is assembled as shown in FIG. 3, a slip gauge 22 of appropriate length is inserted through the hole 40 and allowed to rest upon the anchor head carrier 18. For simple proof load testing, slippage may then be accurately determined by: first, tightening all threaded parts in the assembly to take up any slack between parts, as shown in FIG. 3; next, measuring the extent to which the slip gauge 22 projects above the left hand square nut 14; applying the predetermined proof load to the anchor A by applying a predetermined torque by a torque wrench 26 to the engageable portion 30 of the actuator 12; and then remeasuring the extent to which the slip gauge 22 projects above the left hand square nut 14. The difference between the first and second slip gauge measurements is the total amount of anchor slippage.

Figure 4:
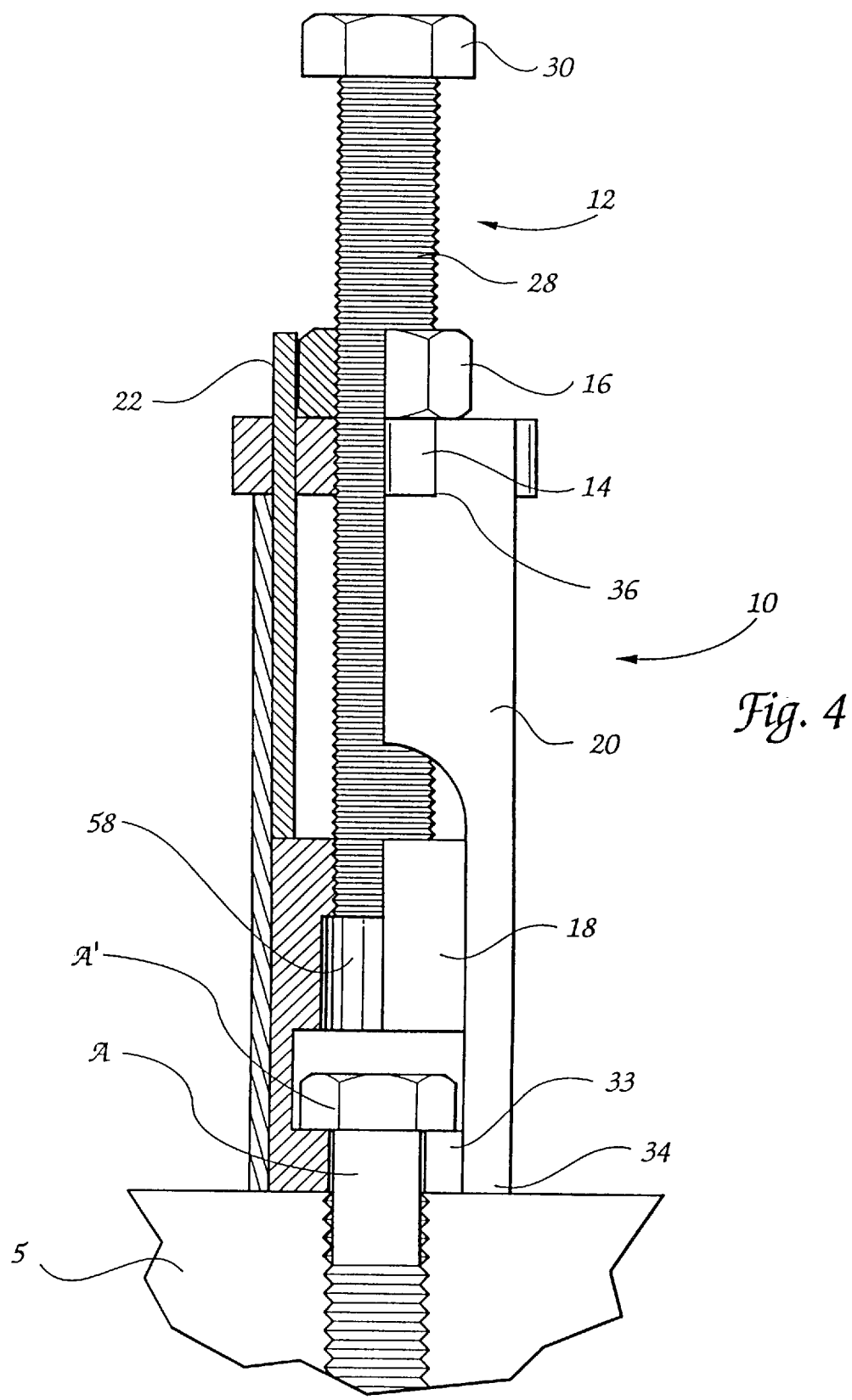
FIG. 4 is a view similar to FIG. 3 with the jam nut in locking disposition.

To determine the total amount of slippage of an anchor A during a sustained load test: first, apply the desired proof load as previously described, but then hand tighten the right hand jam nut 16 against the left hand square nut 14, as shown in FIG. 1, thereby locking all threaded parts together in a fixed position—after locking the threads, any slippage which occurs will result from slippage by the anchor A; then measure the projecting part of the slip gauge; allow the loaded test apparatus to remain in place until the required sustained load period has elapsed, as shown in FIG. 4; after the period of time has elapsed, loosen the right hand jam nut 16 so that the actuator 12 may once again be free to turn; again apply the same proof load as originally applied; if the actuator turns while reapplying the same proof load, the anchor A has slipped, so again measure the projecting part of the slip gauge 22 above the left hand square nut 14. The difference between the two slip gauge measurements, if any, is the total amount of anchor slippage during the sustained loading.

While not essential to variations of the invention, in the preferred embodiment the threaded portion 28 should be cross-threaded, i.e., threaded with dual and opposite threads. By using a left hand single thread 15 in the square nut 14 and a right hand single thread 19 in the anchor head carrier 18, tensile force is applied to an anchor A properly fitted into the flanged slot 32 of the anchor head carrier 18 when the engageable portion 30 of the actuator 12 is rotated in a clockwise direction. If the square nut 14 had a right hand thread and the anchor head carrier 18 had a left hand thread, the engageable portion 30 of the actuator 12 would have to be rotated in a counterclockwise direction in order to apply tensile force to an anchor fitted into the anchor head carrier 18.

Figure 5:
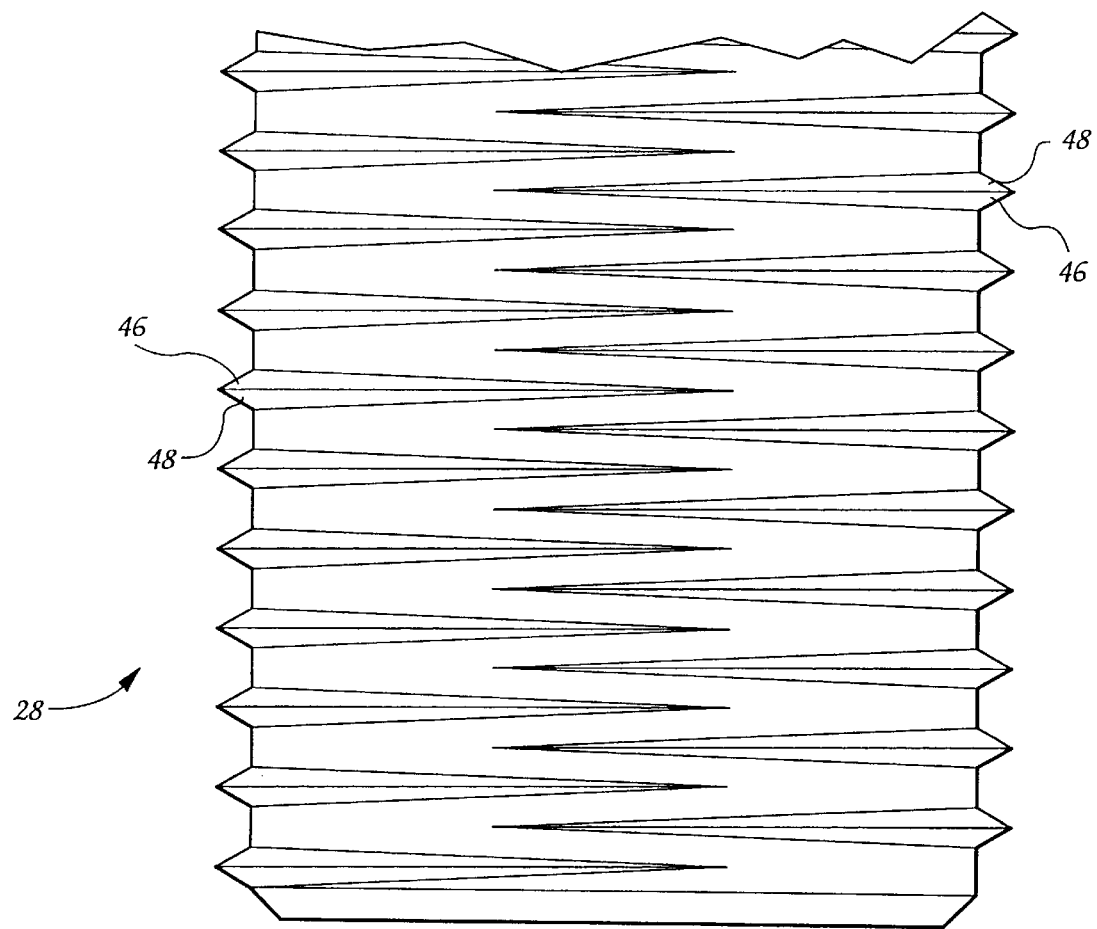
FIG. 5 is an enlarged elevational view of the cross-threaded portion of the actuator of the torque tensile tester of FIG. 1.

Furthermore, since the actuator 12 has both a right hand thread 48 and a left hand thread 46 in transverse relationship that occupy the same threaded portion 28, as illustrated in FIG. 5, the cross-threaded portion 28 of the actuator 12 provides certain mechanical benefits to the present invention that could not be provided by a single, one directional thread. One advantage is that when the actuator 12 is threadedly engaged with two single threaded members of opposite threading, such as the left hand square nut 14 and the right hand anchor head carrier 18, one rotation of the actuator 12 will advance or retract the anchor head carrier 18 by the distance of two times the thread pitch, thereby reducing by one-half the rotational travel required of a torque wrench when a measured load is to be applied. Another advantage is that these two oppositely threaded members, i.e., the left hand square nut 14 and the right hand anchor head carrier 18, eliminate the need for the actuator 12 to bear against another supporting surface, which in turn would increase the total amount of friction present when converting torsional force into tensile force. In the present invention the entire load is supported by the threadedly engageable parts, thereby minimizing frictional resistance to rotation.

Another advantage to the cross-hreaded portion 28 is that the crossthreads reduce the thread form mass of the actuator 12 by an estimated 20% to 25% over the thread form mass of an actuator utilizing a single thread with the same size and pitch, and thus, the threads of actuator 12 of the preferred embodiment exhibits a resistance to shearing under load that is accordingly reduced by 20% to 25%, and a frictional resistance to rotation that is also reduced by an equal amount. The loss of resistance to shearing under load, however, may be compensated for by constructing all threaded parts from tool steel and then appropriately heat treating and tempering them to increase their shear and tensile strength.

Another advantage of the cross-threads over single and opposite threads located opposite each other on an actuator, like tumbuckles, is the compact size of the actuator 12 of the present invention. To use the turnbuckle type of dual right and left hand threads would require a longer, less compact tensile testing apparatus, and furthermore, more friction would develop between threads of mating parts of the turnbuckle style threads because thread form mass would not be reduced as mentioned above. Also, adjustments in length required for coupling to anchors by the anchor head carrier 18 is restricted in the turnbuckle type thread, the adjustments being limited to that point on the actuator shaft where the two threads meet. Adjustments to accommodate conditions of the torque actuated tensile tester 10 of the present invention is limited only by the total length of the threaded portion 28 of the actuator 12.

Integral to the operation of the torque actuated tensile tester 10 must be an acceptable and accurate method of measuring an applied torque in a consistently repeatable way. The conventional torque wrench of any type fulfills this requirement. A torque wrench 26 is applied to the engageable portion 30 of the actuator 12 as illustrated in FIG. 1. This torsional force is converted into a straight line tensile force through the actuator 12 and anchor head carrier 18 which is transmitted to the embedded anchor A. The total applied force is lessened by the frictional resistance of all engaged threads. After subtracting the amount of force which is necessary to overcome frictional resistance, the remaining force is transmitted by way of tensile force to the anchor A, the totality of the tensile force being supported by the left hand square nut 14 which bears upon the top of the castleated housing 20, which transmits a compressive force to the structure S to which the anchor A is affixed in an area circumjacent the embedded anchor A. Thus, the anchor A is effectively pulled in one direction and the structure S to which the anchor A is affixed is pushed against in the opposite direction, and significantly, no torsional force acts upon the anchor A and all generated shear force acts upon the interface of the anchoring structure S and anchor A. Furthermore, the utilization of opposing forces at a frictional interface approximates the actual physical condition of most anchor installations which hold an object, fixture, or machine tightly against the structure to which it is mounted, establishing tensile force acting upon the anchor A and compressive force acting upon the anchoring structure S and generating shear force at the interface of anchor A and structure S.

In determining the relationship between the torque applied and the proof load applied, it is well known that when applying torsional force to produce tensional force in a threaded system, the diameter, thread pitch, thread form, surface finish, lubrication, and material properties all have an effect in the final determination of converted values. Any change in any of these conditions will have a corresponding effect on the results. Formulas for torque-tension relationships for threaded parts and the calculations of frictional resistance are available through INDUSTRIAL FASTENER INSTITUTE and from most manufactures of threaded fasteners. One formula has been found to be reasonably accurate in predicting torque tension ratios:

$$W=T/(K*D)$$

where, W is the actuator tension (lbs), T is the torque applied (inch lbs), K is the coefficient of friction, and D is the nominal diameter of the threaded parts (inches). Generally, where the length of thread engagement between free running mated parts does not exceed the thread root diameter of the male thread, the coefficient "K" will usually fall between 0.15 and 0.20, depending upon whether lubrication is used.

Alternatively, it has been discovered that by coupling the torque actuated tensile tester 10 directly to a dynamometer and applying various torque loads to the apparatus, the resulting tension loads can be read directly from the dynamometer. In this way it is easy to determine directly the tension equivalent of each torque load, the precise repeatability of the apparatus, and the variation, if any, between different types of torque wrenches. By use of a dynamometer, then, the torque actuated tensile tester 10 of the present invention can be calibrated to known values rather than calculated. What emerges from this calibration is a constant numerical value which, when multiplied by the applied torque, reveals the proof load imparted to an anchor.

Figure 6:
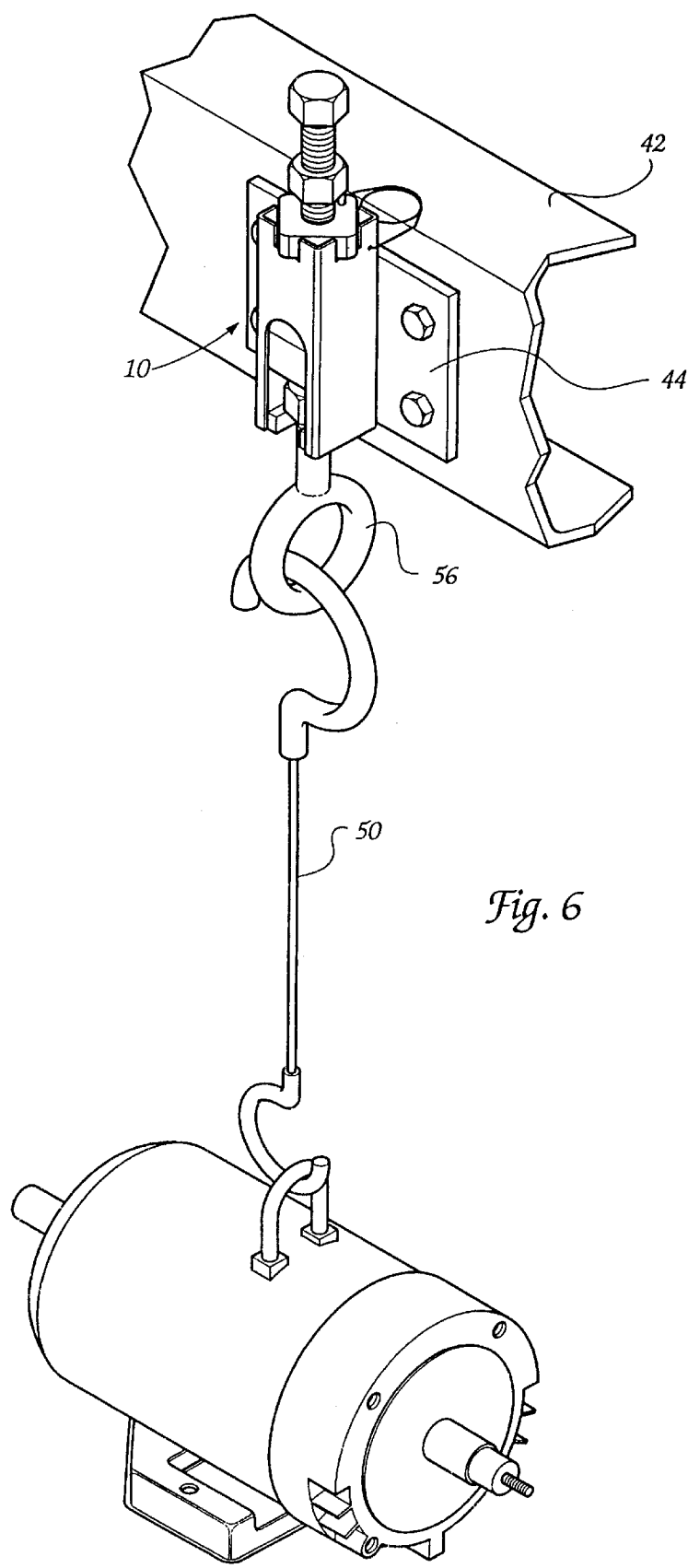
FIG. 6 is a perspective environmental view of the torque actuated tensile tester of FIG. 1 adapted for use to weigh an object.

As mentioned above, the present invention is also well suited for weighing objects. For example, in selecting the proper size, type, and number of fasteners in any anchoring installation, it is helpful to know the weight of the object to be anchored. With some improvision to the housing 20 the weight of an object can be determined on the job site with the torque actuated tensile tester 10. To accomplish this, the housing 20 must be mounted to a fixed structure 42 capable of vertically sustaining the housing 20 when suspending the object to be weighed. As illustrated in FIG. 6, a suitable heavy plate 44 is welded to the housing 20, and the plate is bolted to the fixed structure 42. Alternatively, the assembly may be supported by trestles, a truss, or even on the blades of a fork-lift truck (not shown). Connecting means in the form of a sling 50 can be adapted between the object to be weighed and anchor head carrier 18 of the torque actuated tensile tester 10. For example, an eye 56 can be nested into the flanged slot 32 of the anchor head carrier 18. The actuator 12 is then rotated by means of a torque wrench until the object is vertically lifted and suspended clear of the floor. The torque required to lift the object can be converted into the weight of the object by multiplying the applied torque needed to suspend the object by the constant previously determined by calibration.

The torque actuated tensile tester of the present invention is intended to bring a new reliability and confidence level to the ancient art of anchoring objects. An anchor of any type may be installed and proof load tested with the present invention within a few minutes and at the place where the anchor is permanently to reside. The torque actuated tensile tester can be assembled or disassembled easily and quickly without tools, with ample adjustment capability between threaded parts and the anchor to be tested, and is lightweight, simple to use, and as accurate as the torque wrench which is used in conjunction with it. Tests can be conducted randomly to determine the fitness of anchors or their anchoring structures, or where there are critical load requirements, every anchor can be tested at the job site. If desired or required, old anchors in use for long periods of time can be tested. Sustained load testing to determine if an anchoring structure and an anchor are capable of supporting a given load over a period of times is just as easily conducted at the job site. Ultimate load testing can also be conducted at the job site by continually increasing the torque load until failure occurs. After testing, any anchor may be marked, color coded, tagged, or otherwise specifically identified with the date, applied test load, type of test, who conducted the test, etc., for future reference. In sum, anchor testing can now be easily moved from the laboratory to the job site where testing should be conducted.

It will therefore be readily understood by those persons skilled in the art that the present invention is susceptible of a broad utility and application. Many embodiments and adaptations of the present invention other than those herein described, as well as many variations, modifications and equivalent arrangements will be apparent from or reasonably suggested by the present invention and the foregoing description thereof, without departing from the substance or scope of the present invention. Accordingly, while the present invention has been described herein in detail in relation to its preferred embodiment, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

I claim:

1. A device for proof loading an anchor fixed in a structure, comprising:

an actuator having at least one threaded portion and a portion engageable by a torque applying member;

a support member that is positionable to be rigid with respect to the structure in which the anchor to be proof loaded is affixed;

means on said support member for supporting said actuator for rotation in alignment with the anchor to be proof loaded; and means for engaging the anchor to be proof loaded, said engaging means being movable with respect to said support member and connected to said actuator for rotation of said actuator with respect to the anchor to be proof loaded, said engaging means locatable at a spacing from said supporting means, at least one of said at least one threaded portion of said actuator threadedly engaging at least one of said supporting means and said engaging means for movement of said engaging means toward said supporting means upon rotation of said actuator in one direction by application of a torque to said engageable portion of said actuator by a torque applying member;

whereby, upon engagement of the anchor to be proof loaded by said engaging means and application of a predetermined torque to said engageable portion of said actuator by a torque applying member, a predetermined proof load is applied to the anchor.

2. A device for proof loading an anchor according to claim 1, wherein: said support member has an end that is positionable adjacent the anchor to be proof loaded and that is engageable with the structure in which the anchor to be proof loaded is affixed, and said supporting means is located at a spacing from said end of said support member.

3. A device for proof loading an anchor according to claim 2, further comprising means supported on one of said supporting means and said engaging means and movable with respect to the other of said supporting means and said engaging means for indicating an extent of movement of said engaging means with respect to said supporting means.

4. A device for proof loading an anchor according to claim 2, wherein at least one of said at least one threaded portion of said actuator is threadedly engageable with said supporting means.

5. A device for proof loading an anchor according to claim 2, wherein at least one of said at least one threaded portion of said actuator is threadedly engageable with said engaging means.

6. A device for proof loading an anchor according to claim 2, wherein at least one of said at least one threaded portion of said actuator is threadedly engageable with said supporting means, and wherein at least one of said at least one threaded portion of said actuator is threadedly engageable with said engaging means.

7. A device for proof loading an anchor according to claim 2, wherein said supporting means and said engaging means are oppositely threaded, and at least one of said at least one threaded portion of said actuator is crossthreaded with left hand and right hand threads and is threadedly engageable with said supporting means and said engaging means.

8. A device for proof loading an anchor according to claim 2, further comprising means for locking said actuator in a fixed position with respect to said supporting means to sustain a fixed proof load on the anchor over an extended period of time.

9. A device for proof loading an anchor according to claim 8, wherein at least one of said at least one threaded portion of said actuator is threadedly engageable with said locking means and at least one of said at least one threaded portion of said actuator is threadedly engageable with said supporting means, and said locking means is oppositely threaded with respect to said supporting means for threadedly locking said locking means and said actuator to said supporting means when said locking means is adjacent said supporting means.

10. A device for proof loading an anchor according to claim 2, wherein said support member is an elongated housing.

11. A device for proof loading an anchor according to claim 10, further comprising means engageable with said housing for securing said actuator, said supporting means, and said engaging means to said housing when said housing is inverted.

12. A device for proof loading an anchor fixed in a structure, comprising:
an actuator having an elongated threaded portion and a portion engageable by a torque applying member, said threaded portion being cross-threaded with left hand and right hand threads;
an elongated housing having a first end and a second end, said first end being positionable circumjacent the anchor to be proof loaded and engageable with the structure in which the anchor to be proof loaded is affixed;
a first nut that is attachable to said second end of said housing, said first nut being threaded in one direction and threadedly engageable with said threaded portion of said actuator for supporting said actuator for rotation in alignment with the anchor to be proof loaded; and
means for engaging the anchor to be proof loaded, said engaging means being threaded in a direction opposite said one direction and threadedly engageable with said threaded portion of said actuator for rotation of said actuator with respect to the anchor to be proof loaded, said engaging means locatable at a spacing from said first nut;
whereby, upon engagement of the anchor to be proof loaded by said engaging means and application of a predetermined torque to said engageable portion of said actuator by a torque applying member, said engaging means is urged towards said first nut and a predetermined proof load is applied to the anchor.

13. A device for proof loading an anchor according to claim 12, further comprising a second nut having a thread in a direction opposite said one direction and threadedly engageable with said threaded portion of said actuator for threadedly locking said second nut and said actuator in a fixed position with respect to said first nut when said second nut is adjacent said first nut on said actuator, whereby a proof load can be sustained to the anchor over an extended period of time.

14. A device for proof loading an anchor according to claim 13, further comprising a slip gauge for indicating movement of said engaging means with respect to said first nut, wherein said first nut has a hole and said slip gauge is slidably extendable through the hole in said first nut and is movable with said engaging means.

15. A device for proof loading an anchor according to claim 14, further comprising a keeper clip having two end portions, said housing having two holes, and said two end portions of said keeper clip extendable through the two holes in said housing for securing said first nut, said engaging means, and said actuator to said housing when said housing is inverted.

16. A device according to claim 15, further comprising a torque applying member, wherein said torque applying member is a torque wrench.

17. A device for measuring the weight of an object to be anchored to an anchor fixed in a structure, comprising:
an actuator having at least one threaded portion and a portion engageable by a torque applying member;
a support member having an end that is positionable adjacent an anchor fixed in a structure and that is engageable with the structure in which the anchor is affixed;
means on said support member for supporting said actuator for rotation in alignment with the anchor, said supporting means located at a spacing from said end of said support member;
means for engaging the anchor, said engaging means connected to said actuator for rotation of said actuator with respect to the anchor, said engaging means locatable at a spacing from said supporting means, at least one of said at least one threaded portion of said actuator threadedly engaging at least one of said supporting means and said engaging means for movement of said engaging means toward said supporting means upon rotation of said actuator in one direction by application of a torque to said engageable portion of said actuator by a torque applying member;
means on said support member for fixedly mounting said support member above the object to be weighed; and
means for connecting said engaging means to said object to be weighed;

whereby, upon engagement of the object to be weighed by said connecting means, the application of a torque to said engageable portion of said actuator by a torque applying member causes the engaging means to move towards the supporting means to suspend the object to be weighed, the torque applied to suspend the object being directly proportional to the weight of the object.

18. A device for determining the weight of an object, comprising:

an actuator having at least one threaded portion and a portion engageable by a torque applying member;

a support member attachable to a fixed structure;

means on said support member for supporting said actuator for rotation about a vertical axis; and means for engaging the object to be weighed, said engaging means being movable with respect to said support member and connected to said actuator for rotation of said actuator with respect to the object to be weighed, said engaging means locatable at a spacing from said supporting means, at least one of said at least one threaded portion of said actuator threadedly engaging at least one of said supporting means and said engaging means for movement of said engaging means toward said supporting means upon rotation of said actuator in one direction by application of a torque to said engageable portion of said actuator by a torque applying member;

whereby, upon engagement of the object to be weighed by said engaging means, the application of a torque to said engageable portion of said actuator by a torque applying member causes the engaging means to move towards the supporting means to suspend the object to be weighed, the torque applied to suspend the object being directly proportional to the weight of the object.

19. A device for weighing an object according to claim 18, wherein at least one of said at least one threaded portion of said actuator is threadedly engageable with said supporting means.

20. A device for weighing an object according to claim 18, wherein at least one of said at least one threaded portion of said actuator is threadedly engageable with said engaging means.

21. A device for weighing an object according to claim 18, wherein at least one of said at least one threaded portion of said actuator is threadedly engageable with said supporting means, and at least one of said at least one threaded portion of said actuator is threadedly engageable with said engaging means.

22. A device for weighing an object according to claim 18, wherein said supporting means and said engaging means are oppositely threaded, and at least one of said at least one threaded portion of said actuator is cross-threaded with left hand and right hand threads and is threadedly engageable with said supporting means and said engaging means.

* * * * *